United States Patent [19]

Noakes et al.

[11] Patent Number: 4,795,330

[45] Date of Patent: Jan. 3, 1989

[54] APPARATUS FOR PARTICLES

[75] Inventors: Timothy J. Noakes, Nr Alton; Ian D. Pavey, Haslemere; Stuart C. Ord, Westminster Park, all of England

[73] Assignee: Imperial Chemical Industries PLC, London, England

[21] Appl. No.: 17,423

[22] Filed: Feb. 24, 1987

[30] Foreign Application Priority Data

Feb. 21, 1986 [GB] United Kingdom ................ 8604328

[51] Int. Cl.$^4$ ............................................. B22D 11/01
[52] U.S. Cl. .................... 425/6; 425/174.8 E; 264/10; 264/22; 361/228; 239/3
[58] Field of Search ............ 425/6, 174.8 R, 174.8 E; 239/3; 264/10, 26; 361/227, 228

[56] References Cited

U.S. PATENT DOCUMENTS

| | | | |
|---|---|---|---|
| 2,302,289 | 11/1942 | Bramstock-Cook | 239/3 |
| 2,525,347 | 10/1950 | Gilman | 55/107 |
| 2,810,426 | 10/1957 | Till et al. | 425/174.8 E |
| 4,264,641 | 4/1981 | Mahoney et al. | 427/30 |

FOREIGN PATENT DOCUMENTS

| | | | |
|---|---|---|---|
| 37769 | 11/1971 | Japan | 264/10 |
| 18405 | 5/1972 | Japan | 118/621 |
| 550022 | 6/1974 | Switzerland | 264/10 |

*Primary Examiner*—Bernard Nozick
*Attorney, Agent, or Firm*—Cushman, Darby & Cushman

[57] ABSTRACT

A process for the production of solid particles, characterized by the solidification in flight of an electrically charged spray of fluid droplets of narrow particle size distribution, and an apparatus for that process comprising a sprayhead with a channel for the fluid communicating with an outlet; means for subjecting the fluid to an electrical field such that the fluid will move from the sprayhead under the influence of the field to produce a spray of the fluid, the means including means for applying a first potential to the fluid; an electrode mounted spaced from but adjacent to the sprayhead with means to apply a second potential to that electrode; and a spray chamber, so positioned that in use the sprayhead delivers the spray to the chamber interior, and provided with means to apply a third potential to the chamber, and so dimensioned and arranged that in use the majority of the spray droplets solidify before impinging on any surface of or within the chamber.

6 Claims, 5 Drawing Sheets

APPARATUS FOR PARTICLES

This invention relates to a process and apparatus for producing solid particles by means of a solidifying spray.

It is desirable for a number of industrial applications to produce particulate materials with a narrow size distribution range. Examples of such fairly uniform particles include organic polymer or oligomer particles for further processing, such as for even solution and/or dispersion in inks, paints, adhesives and other surface coatings, and in solution/dispersion spinning, and for ready processing in sintering and melt extrusion spinning or moulding.

The electrostatic apparatus described in GB-A-No. 1,569,707 is characterized by a field intensifying electrode near a charged sprayhead, and produce a charged spray of liquid droplets which are accelerated by the applied electrostatic field, generally to impinge on and be discharged at an earthed target surface. The droplets produced by such apparatus characteristically have a narrow size distribution range i.e. are fairly uniform.

We have found that it is possible to produce in this manner a charged spray of droplets which are subjected to a solidifying process in flight, for example by cooling of a melt spray, solvent loss from a solution of a solid solute, or reaction initiated in a single species or between a mixture of species.

In one aspect the present invention therefore provides a process for the production of solid particles, characterised by the solidification in flight of an electrically charged spray of fluid droplets of narrow particle size distribution. Apparatus for this process forms a second aspect of the present invention described and claimed in greater detail hereinafter.

In the foregoing process the applied electrostatic field will tend to accelerate the charged solidifying particles up towards a terminal velocity against the viscous drag of the ambient gas (often air), and towards any adjacent earthed surface. If the mean flight time is shorter than the mean solidification time of the particles, the particles will disadvantageously tend to coalesce on the target surface, precluding the collection of discrete solid particles.

We have found that to some extent this may be avoided by increasing the mean flight time for a given mean particle size. The flight time may be adjusted by adjusting the field potential gradient, e.g. by increasing the flight path for a given potential difference between sprayhead and target, or by decreasing the potential difference for a given flight path.

The mean flight time may also be increased by decreasing the mean particle size (and hence the mean terminal velocity) for a given mean flight path. Particle size is largely independent of the mean flight path and potential gradient, but can be controlled by adjusting the resistivity, viscosity and flow rate of the sprayed liquid, and increasing the voltage on the sprayhead. However, it will be seen that adjusting the sprayhead voltage tends to vary both flight time and particle size so that increasing the flight path may be the only practical option. If larger particles are desired it may be necessary to extend the flight path to an inconvenient degree.

We have found that the foregoing problems may be solved by at least partly discharging the solidifying spray.

Thus in a third aspect the present invention provides a preferred process for the production of an electrically charged spray of fluid droplets of narrow particle size distribution, by the at least partial discharge of the spray, and by the solidification in flight of the spray droplets, Apparatus for this preferred process forms a fourth aspect of the present invention, described and claimed in greater detail hereinafter.

In the process of the present invention, the spray may be a single fluid or a mixture of multiple components which interact or may react to give the solidified particulate product. The spray may be a solution, dispersion, suspension or melt of the product material or of a precursor or precursors of the product material.

If a single fluid precursor, the precursor will solidify, (e.g. cool, lose liquid vehicle by evaporation, or react with itself) after leaving the sprayhead (as necessary after external activation) to form the product particles. Multiple precursor components will interact and/or react mutually and solidify similarly after leaving the sprayhead(s).

Fluids of interest are more fully discussed hereinafter.

Where a single fluid is sprayed in accordance with the present invention only a single sprayhead is necessary. When a plurality of fluids (for example two) is sprayed, this may be achieved either by (a) multiple single sprayheads arranged so that the e.g. two fluids are mutually contacted in flight, or
(b) a single sprayhead with multiple feeds and outlets to give pre-flight, point-of-flight or in-flight contact of the fluids.

In use of course the or each sprayhead is charged to a potential different from that of the substrate and that of the field intensifying electrode, the former of which is generally at earth potential. An electrical field is thus set up between the sprayhead and the earthed substrate and the field intensifying electrode, and fluid sprayed from the sprayhead acquires the charge of the sprayhead and is attracted towards any adjacent surfaces at earth potential. In general, the field intensifying electrode in its position adjacent to the sprayhead does not affect the field to the extent that it becomes a target. The substrate is generally placed to be the closest earthed surface in the spray 'line of fire' and most, if not all, of the spray will be attracted to impinge on the substrate.

In its second aspect, the present invention uses an apparatus for the production of solid particles by the production and solidification in flight of a spray of solidifiable fluid droplets of narrow particle size distribution comprising: a sprayhead with a channel for the fluid communicating with an outlet; means for subjecting the fluid to an electrical field such that the fluid will move from the sprayhead under the influence of the field to produce a spray of the fluid, the means including means for applying a first potential to the fluid; an electrode mounted spaced from but adjacent to the sprayhead with means to apply a second potential to that electrode; and a spray chamber, so positioned that in use the sprayhead delivers the spray to the chamber interior, and provided with means to apply a third potential to the chamber, and so dimensioned and arranged that in use the majority of the spray droplets solidify before impinging on any surface of or within the chamber.

The third potential is generally at or near earth potential.

When spraying with the third potential at earth potential, the first potential may be $\pm 1$ to 20 KV and the second potential may be at or near earth potential, as disclosed in our UK Specification No. 1,569,707.

The first potential may also be ±25 to 50 KV, and the second potential ±10 to 40 KV.

For the latter set of working potentials, the electrode preferably comprises a core of conducting or semi-conducting material sheathed in a material of dielectric strength and volume resistivity sufficiently high to prevent sparking between the electrode and the sprayhead and volume resistivity sufficiently low to allow charge collected on the surface of the sheathing material to be conducted through that material to the conducting or semi-conducting core. Suitably, the volume resistivity of the sheathing material is between $5 \times 10^{11}$ and $5 \times 10^{13}$ ohm.cm, the dielectric strength of the sheathing material is greater than 15 KV/mm and thickness of the sheathing material is 0.75 to 5 mm, preferably 1.5 to 3 mm.

Sheathed electrodes typically using the latter potentials above are of particular use in spraying at high flow rates, as disclosed in the reference specifications. It is believed, e.g. that practicable or convenient production speeds for organic polymer products may well require such high flow rates, and therefore the use of this particular apparatus embodiment.

Preferably the electrode is adjustably mounted to permit ready variation in relative positions of the sprayhead and electrode.

The spray may be diffused by placing the electrode upstream of the emerging spray or focused by placing it downstream of the emerging spray.

In the above apparatus with single sprayhead(s) the, or each, single sprayhead may have any of the forms conventionally used for the atomisation of a fluid in an electrostatic field. Thus at the end of the feed conduit the sprayhead may have a nozzle orifice (generally circular), an annular slot (for example formed by a circular aperture with a concentric core) or a rectangular ('linear') slot. Circular orifices or annular slots in the face of a broadly conical outlet face (as described hereinafter for multiple outlet spayheads) are among preferred sprayhead outlets. Preferred sprayhead outlets for higher throughput rates include elongate linear slots which may be up to 3 m long for example 0.5 to 1 m. Linear slots may be curved convexly or concavely along their length. All these apertures are preferably of capillary cross dimensions, e.g. 0.05 to 0.5 mm, to assist atomization. Similarly, it is preferred that the apertures are defined by sharp edges, which may additionally be toothed, so that the field intensity at the sprayhead surface, and hence the atomisation, is enhanced.

In view of the proximity of the electrode to the sprayhead it is often convenient that the electrode follows the shape of the fluid outlets, e.g. twin parallel bars, or a plate with a wider slot, by a slot, or an annulus or torus by a circular nozzle or annular slot.

Atomization may in some instances be assisted by a forced gas stream with (or across) the issuing spray, as in UK No. 1569707. In some cases this stream may have further advantages, for example, if heated, as a thermal initiator for some free-radical curing polymers. However, if passed against the issuing spray at a suitably low velocity, such a stream may be used more usefully to prolong the mean flight time of the solidifying particles.

In another embodiment of this aspect, the present invention uses an apparatus for the process of the first aspect of the invention wherein the spray is a mixture of a plurality of fluids (in particular the precursor components of a multi-component organic polymer) comprising:

a sprayhead with a plurality of channels for said fluids each communicating with an outlet;

means for subjecting the fluids at the outlets to an electrical field, such that the fluids will move from the sprayhead under the influence of the field, to produce a spray of the fluids, the outlets being so disposed that the fluids mix on or whilst moving from the sprayhead, and the means including means for applying a first potential to at least one of the fluids;

an electrode mounted adjacent to the sprayhead with means to apply a second potential to that electrode, and a spray chamber, so positioned that in use the sprayhead delivers the spray to the chamber interior, provided with means to apply a third potential to the chamber, and so dimensioned and arranged that in use the majority of the spray droplets solidify before impinging on any surface of or within the chamber.

When a plurality of fluids is sprayed from such a single sprayhead with multiple feeds, these feeds may conveniently end in closely adjacent orifices or slots (for example parallel rectangular slots) or a closely adjacent coaxial circular orifice and annular slot(s) or similarly coaxial annular slots. Mixing of the components as sprays occurs at the point of flight, or during flight.

As for single outer sprayheads, sharp, optionally toothed, edges and a forced gas stream may be advantageous.

Elongate linear slots of the type described for single outlet sprayheads are among preferred outlets for higher throughput rates.

Where the feeds end in closely adjacent parallel slots of any length, the feeds are conveniently in the form of channels between parallel plates.

Good mixing of two components is achieved where such a sprayhead comprises four such plates, two inner and two outer, defining three channels. Suitably, the plates are symmetrical about the central channel, the edges of the plates by the outlet slots are chamfered towards the central outlet and the central outlet is located downstream of the two outer outlets, to give a broadly sphenoidal (i.e. wedge-shaped) outlet edge of the sprayhead.

Suitably the included angle of the chamfers or bevels on the inner plates is less than the included angle of the bevels on the outer plates, being respectively preferably in the ranges 10° to 60° and 80° to 150°.

In use one component fluid is run down the central channel, and the other is run down the two outer channels.

A three-plate two-channel sprayhead may also be used, with the central plate having two opposing bevels as described above for the two inner plates, and the sprayhead is also generally sphenoidal.

The edges of the plates may be convexly or concavely curved along their length.

Similarly, where for two components the feeds end in a closely adjacent circular orifice and a coaxial annular slot, these feeds are conveniently in the form of a central tube bore and a channel defined by that tube and a coaxial outer tube interior. Again, good mixing is achieved when the outlet ends of the tubes are symmetrical about the common tube axis and chamfered towards the central outlet and the central outlet is downstream of the outer outlet, to give a broadly conical outlet face of the sprayhead.

Suitable and preferred include angles of the bevelled edges of the tubes are as described for the analogous plates hereinbefore.

In use one fluid component is run down the central channel, and the other is run down the outer channel.

Considerations of working potentials and the nature, shape and use of the electrode are as for single sprayheads hereinbefore.

The orientation of any of the above sprayheads in use is in general not critical, although in the most convenient embodiments the sprayhead sprays downwards and the spray is allowed to fall under gravity and any applied electrical or mechanical (e.g. gas stream) field.

In all the foregoing sprayheads (single and multiple) suitable means for subjecting the fluids at the outlet(s) to an electrical field include a chargeable, e.g. metal electrode in the sprayhead in contact in use with at least one of the fluids (and preferably both or all) either at the outlet(s) (for example a conducting or semi-conducting sprayhead outlet surface) or a short distance upstream thereof (for example as a buried electrode within a non-conducting sprayhead).

Any appropriate method of producing the desired potential may be used, for example transformed and rectified mains supplies or a van der Graaf generator.

The field intensifying electrode may for example be run off an inductive or resistive tap off a transformed mains sprayhead supply.

Conventional insulation precautions must of course be taken for all points at other than earth potential.

The average size of the atomised droplets in general may be controlled by the position of the field intensifying electrode in relation to the sprayhead. For example, for a given flow rate of liquid, bringing the electrode closer to the sprayhead results in the droplets generally being of a smaller average size.

Suitable such parameters for desired particle sizes of given materials are a matter of routine trial.

By controlling the position of the electrode a selected size of droplets may be produced suitable for a particular use. For example, large numbers of small particles (e.g. 20–30 micron diameter) may be preferred for ready solution/dispersion in inks, paints and surface coatings.

The apparatus may also comprise one or more auxiliary electrodes to further influence the spray shape and position ('pattern'), without being close enough to the sprayhead to significantly affect the spraying potential. For example the spray chamber may define an elongate central flight path for the solidifying spray droplets and may be provided with e.g. toroidal auxiliary electrodes about the flight path at suitable potentials such that the solidifying spray droplets, subject to conventional gravitational and/or the applied electrostatic forces are repelled from the chamber walls towards the central flight path.

Accordingly in a further embodiment of its first aspect, the invention provides a process of the first aspect characterised in that the distribution of the electrostatic field is controllably modified by at least one auxiliary electrode as defined.

The shape and location of and relative potential on the auxiliary electrode(s) all affect the spray pattern. A variety of patterns may be achieved in this way, and accordingly these parameters may vary between wide limits, depending as they do on the same parameters inter alia as do the field potential and flight path/time (q.v.), and suitable values may similarly be readily determined by routine trial.

Each electrode may be in any suitable shape e.g. straight, curved or annular metal rods, or flat, curved, dished, cylindrical or partly or fully toroidal grids of the same rodding. Such electrodes may be connected in a network at different locations but at the same potential, or may be held at different potentials. For the spraying parameters mentioned hereinbefore, straight, curved or annular steel rods of 1 to 10 mm diameter and 50 mm to 5 m in length or annular diameter may be used either singly or arranged to form a planar, curved or cylindrical grid of straight rods, a curved or dished grid of curved rods, or a cylindrical or partly or fully toroidal grid of annular rodding, in each case with a mean spacing of 10 to 100 mm between rods.

Each auxiliary electrode may be at the same potential as, or at a potential intermediate between those of the sprayhead and the substrate; for example a substrate at $\pm 1$ to $\pm 20$ KV with respect to the sprayhead a field intensifying electrode at the same potential as the substrate and an auxiliary electrode at $\pm 0.25$ to $\pm 10$ KV, or a substrate at $\pm 25$ to 50 KV with respect to the sprayhead, and a field intensifying electrode at $\pm 10$ to 40 KV. This may be achieved by for example running the auxiliary electrode off an inductive or resistive tap off the sprayhead supply, or off a separate supply.

A wide variety of materials may be produced in accordance with the present invention, including organic oligomer and polymer particles. The latter may (depending on the intended application) may be thermoplastic or thermoset and may be capable of (further) crosslinking or not. Organic oligomer or polymer particles are generally produced from sprays of room-temperature liquids which are, or are solutions, dispersions or suspensions of, oligomers, polymers or reactive oligomer or polymer precursors as convenient. Any solvent or vehicle may be inert or it may react with any reactive component(s) of the sprayed fluid.

The sprayed fluids should in general have a volume resistivity in the range $10^6$ to $10^{12}$ ohm. cm, preferably $10^7$ to $10^{10}$ ohm. cm.

Generally the low shear rate viscosity at the spraying temperature of the sprayed fluid(s) should be less than 40 poise, preferably 0.005 to 10 poise for example between 0.5 to 5 poise, although it is a surprising feature of the present invention that fluids with viscosities in excess of 5 poise (and even in excess of 30 poise) may be satisfactorily sprayed to give good coats particles.

The spraying temperature of the fluid(s) may be any compatible with the fluid(s) or its/their solidification rate. Temperatures from 0° to 180° C. for example 15° to 150° C. may be used.

The suitablility of any given material which within the foregoing constraints can be sprayed using the apparatus of the present invention will largely be determined by the desired particle sizes and the solidification rate of the droplets. This general point may be illustrated with reference to the most convenient apparatus embodiment where the charged or undischarged spray falls directly downwards. In both cases the droplets/particles tend to be accelerated in a short distance to a terminal velocity in the ambient gas under gravity and in the case of undischarged droplets/particles also under the applied electric field. For a discharged spray, the particle size determines the terminal velocity, which in turn is the dominant factor in determining (a) the necessary flight time, and hence rate of solidification, for a given fall, or (b) the fall necessary for a given solidification time and rate (i.e. rate of cooling, vehicle loss or reaction)

The correlation between discharged particle size and terminal velocity is well known, as is its rapid increase with particle size, as the appropriate figures below show:

| particle size micron | terminal velocity mm. sec$^{-1}$ |
|---|---|
| 30 | 24 |
| 60 | 94 |
| 100 | 239 |
| 140 | 405 |
| 200 | 680 |
| 260 | 1000 |

From these data the maximum solidification time for a given fall may readily be calculated. For example for a 2 or 20 m fall. The following times apply:

| particle size micron | approximate maximum solidification time, sec. (min) | |
|---|---|---|
| | 2 m | 20 m |
| 30 | 80 | 800(13+) |
| 60 | 20 | 200(3+) |
| 100 | 8 | 80 |
| 140 | 5 | 50 |
| 200 | 3 | 30 |
| 260 | 2 | 20 |

The potential limits on solidification rates (and hence processable materials) and on particle sizes will thus readily be seen. For undischarged sprays the terminal velocity will tend to be higher and due adjustment will need to be made in the relevant calculations.

Typically convenient falls for industrial production will tend to vary in the range of 1.5 to 30 m from pilot to full scale plant and particle sizes of greatest interest from 30 to 300 micron. With these parameters the maximum solidification time may vary from 0.5 sec to 20 min. Within these ranges falls of 5 to 10 m and particles of 100 to 2-0 micron give rise to times of 5 to 40 sec. The choice of drop (and hence plant scale) and of suitable materials for processing will be evident to the skilled man.

The foregoing suitable materials include monomer and oligomer precursors of organic oligomers and polymers respectively. These precursors may in flight be homo-oligomerised or -polymerised or as feasible, or co-oligomerised or -polymerised with other species. Such precursors include olefinic materials (i.e. which are or comprise olefinic monomers) such as acrylics, and precursors of conventional unsaturated polyester-olefinic copolymers, polyurethanes and polyureas and thiolenes, and heterocyclic precursors.

Olefinic species may in general, in addition to being homo-oligomerised or -polymerised, be co-oligomerised or -polymerised with other olefinic species.

In addition to acrylics olefinics include halo-and aryl-olefinics.

Acrylics include materials which are or comprise unsaturated carboxylic ('vinylic') acids and esters either alone or as capping units. Examples of the latter include:

polyester acrylics with optional backbone unsaturation, acrylics based on isocyanates and homo- and co-oligomers thereof, and polyurethanes, polyureas and polyurethane-polyureas, and functionalised acrylics i.e. acrylic backbones capped by acrylics, Polyurethanes/polyureas include the above species named for acrylics.

Hetrocyclic precursors include epoxides.

Thiolene precursors include thiols.

Whether the materials are most suitably sprayed using a single outlet sprayhead, or a twin outlet sprayhead or two single outlet sprayheads will depend on the type of reactive system used.

Systems which may be applied from a single outlet sprayhead include any material (a) which does not react in flight, (b) reacts in flight, where reaction is externally initiated at the sprayhead or in flight.

Category (a) includes cooling melts and solutions, dispersions or suspensions losing vehicle.

Within category (b) the external initiation may be radiation curing, i.e. by radiation such as microwave, uv, visible, ir, electron beam or sonic, or chemical such as in anaerobic curing materials.

Radiation curing systems are essentially free-radical curing systems, which may be initiated on or in flight. All the free-radical materials described above for multi-component systems may be used, i.e. olefinics, including acrylics, and precursors of unsaturated polyester-olefinics and thiolenes.

The single sprayed fluid will contain all the desired monomers and/or oligomers and a conventional catalyst/initiator which itself is initiated by the relevant radiation. For example, suitable uv curing catalysts include benzophenone-amine systems.

Systems which need to be applied from a twin outlet sprayhead or two single outlet sprayheads include (a) two components systems where the components react on mixing, or (b) systems where catalysis is chemically initiated by a spray component, e.g. a (catalyst+promoter) system.

Category (a) includes precursors for polyurethanes/-polyureas and thiolenes, and heterocycles. The desired monomers and or oligomers are distributed as apt between the outlets or sprayheads.

Category (b) includes free-radical curing systems of the type described above for a single outlet sprayhead. Many of these materials may also be used in conventional group-transfer curing systems. Typically the desired catalyst and promoter are distributed between the outlets or sprayheads, as are the desired monomers and/or oligomers as apt.

In its third aspect the present invention provides a preferred process for the production of solid particles by producing an electrically charged spray of fluid droplets of narrow particle size distribution, by at least partially discharging the spray, and by the solidification in flight of the droplets.

GB-B No. 2,018,627 describes at least partial ionic (corona) discharge of a charged spray using an earthed spike near the sprayhead. However, in the process using the apparatus of the second aspect of the invention to produce a fairly uniform spray (and hence product particles), we have found that the corona discharge tends to deleteriously affect the formation of the spray itself. We have now surprisingly found that use of field intensifying electrode in the form of a shield electrode between the spray head and a sharp discharge electrode solves this problem.

Thus, in its fourth aspect the present invention provides an apparatus for the production of a solid particle by producing an electrically charged spray of fluid droplets of a narrow particle size distribution, by at least partial discharge of the spray, and by the solidification in flight of the droplets, the apparatus comprising:
  a sprayhead with a channel for the fluid communicating with an outlet,
  means for subjecting the fluid to an electrical field such that the fluid will move from the sprayhead outlet under the influence of the field to produce a spray of the fluid, the means including means for applying a first potential to the fluid;
  and a shield electrode mounted spaced from but adjacent to the sprayhead with means to apply a second potential to that electrode,
  a sharp discharge electrode; and
  means for applying a third potential of opposite polarity to the first potential to the discharge electrode, such as to produce a corona to discharge the spray,
  the shield electrode having an orifice through which fluid from the sprayhead can issue towards the discharge electrode, and the shield electrode and the orifice being so positioned and dimensioned as to shield the sprayhead in use from the corona.

To provide the desired shielding effect, the orifice in the shield electrode must be quite small. We found it surprising that the spray did not merely deoposit on the shield electrode. We found it is possible to chose an orifice size which is large enough to allow the spray of droplets through without substantial deposition on the shield electrode, whilst at the same time is small enough to prevent the corona reaching the sprayhead; this is described further below. In general, however, insofar as is compatible with its purpose, it is often desirable that the orifice conforms to the shape of the fluid outlet(s) e.g. a wider slot. The conformation of the shield electrode to achieve shielding is described fully hereinafter in the specific description of such apparatus.

The second (shield electrode) potential may be at or near earth potential.

The first potential may then suitably be as correspondingly described for the first potential using the same second (field intensifying electrode) potential in the second aspect of the present invention (undischarged spray process). In practice we have found that in these conditions the third potential needs to be of opposite polarity to the sprayhead first potential (and hence of the spray droplets potential) to induce corona discharge of the spray to any adequate extent.

The shield electrode should be sufficiently conducting to remove any charge acquired from the discharge process; subject to this it may be of a conductor, e.g. a metal, or a semi-conductor, as described below.

For the reasons described hereinbefore for the second aspect process, the first and second potentials may be increased in the same polarity sense with a view to increasing throughput; desirably also the conductivity of the shield electrode surface is decreased, provided it remains sufficiently conductive to remove any charge acquired from the discharge process.

Accordingly, it is believed that, by increasing the second potential to +2 to 15 KV with respect to earth of the same polarity as the sprayhead and using a semiconductive material for (example a semi-conductive plastic or ceramic) with a resistivity of $3 \times 10^2$ to $3 \times 10^4$ ohm. cm as the shield electrode surface, the first potential may be increased from 25 to 40 KV. the shield electrode may consist essentially of such material or the material may sheath a conductive core. If the latter, a dielectric strength of the sheathing material of greater than 8 KV/mm is desirable.

Otherwise, the following process and apparatus parameters in these preferred process and apparatus may suitably be as so decribed for corresponding parameters in the first and second aspects of the present invention:
  the position of the shield electrode with respect to the sprayhead and its adjustability, its use to control droplet/particle size;
  the sprayhead, including the form and dimensions of single and multiple outlets, the sprayhead electrode(s); (apparatus having a sprayhead with multiple outlets is a particular embodiment of this fourth aspect of the invention);
  the means of producing the desired potentials;
  the need for insulation;
  generally, the use, nature shape, dimension, potentials and means of applying auxiliary electrodes; (a process using such electrodes is a particular embodiment of the third aspect of the invention; an apparatus having such electrodes is a particular embodiment of a fourth aspect of the invention);
  the properties, nature and suitablility of sprayhead fluids and specific sprayable materials;
  process temperatures and other conditions.

Figure 1:
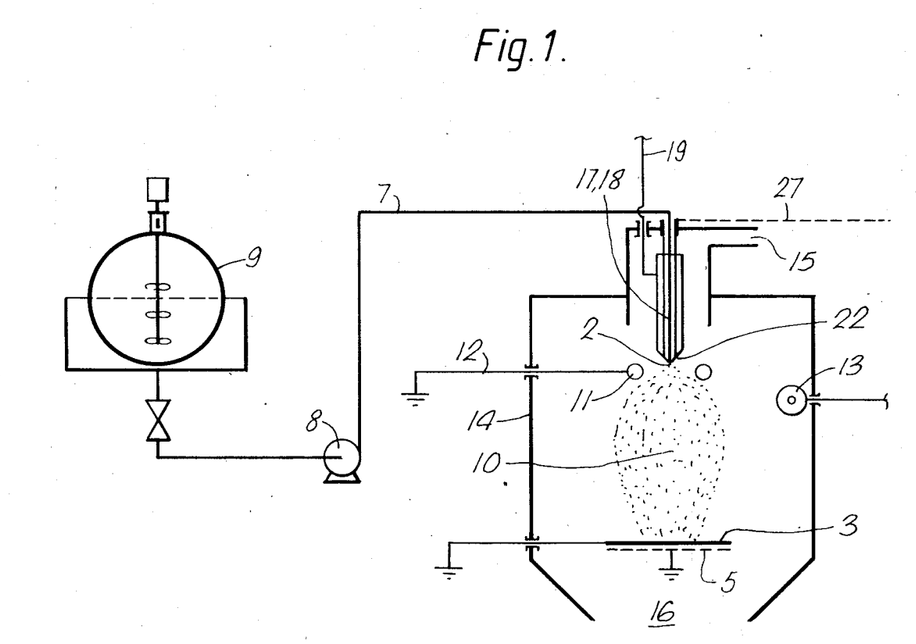
FIGS. 1 to 5 hereinafter show various embodiments of an apparatus for the process of the present invention, FIGS. 3 to 5 showing embodiments of the preferred apparatus of the present invention.

The apparatus shown in FIG. 1 has a sprayhead 1, here comprising a feed conduit 17 running to a conductive circular capillary nozzle 2 of the type described hereinbefore. Mounted coaxially with the nozzle 2 within the feed conduit 17 is a sprayhead electrode 18 with electrical lead 19, providing means to charge the sprayhead 1 to a first potential. The circular nozzle may have a diameter in the range 0.15 to 3 mm, preferably 0.05 to 0.5 mm, to give flow rates of the order of 0.1 to 10 ml/min. The nozzle may also (to increase throughput) be in the form of a linear slot up to about 3 m long of a cross section in the above range. For a circular nozzle an annular field intensifying electrode 11 of 15 to 25 mm diameter is mounted coaxial with and 5 to 25 mm below the nozzle 2. The electrode favourably consists of a core of conducting or semi-conducting material sheathed in a material of dielectric strength greater than 15 KV/mm, volume resistivity between $5 \times 10^{11}$ and $5 \times 10^{13}$ ohm. cm, and thickness 0.75 to 5 mm.

The electrode has an electrical lead 12, here running to earth, and providing means to charge the shield electrode to a second potential.

The sprayhead 1 is mounted at the top of, and so as to spray into, a spray chamber 14, and is directly above a flat substrate 3, which may be for example a belt strung between and rolled on drums 4,4 (not shown).

The spray chamber 14 is not shown to scale. The distance from the sprayhead 1 to the collector substrate 3 may vary according to the necessary process flight time, which will depend in turn on the material to be processed and other process parameters as described hereinbefore. Typically, however, it may be in the range 3 to 90 m, for example 10 to 30 m. The spray chamber may have any convenient lateral dimension, provided that, if it does not comprise or enclose any means to keep the sprayed material off the side walls (e.g. auxiliary electrodes), the chamber 14 is not so narrow that an unacceptable proportion of the sprayed material collects on the side walls rather than on the substrate 3. Where such means are provided of course the chamber 14 may be correspondingly narrower. Within the foregoing constraints the chamber cross-dimensions may typically be in the range 1.5 to 45 m, for example 4.5 to 15 m.

A field electrode 5 behind the substrate 3 is generally unnecessary, as sufficient control of the spray pattern may be achieved if desired by adjusting the potential, size and configuration of the nozzle 2 and the electrode 11 and their relative positions, and by the use of auxiliary electrodes if necessary.

The nozzle 2 is connected via a line 7 containing pump 8 to a reservoir 9 for the material to be sprayed.

The apparatus of FIG. 1 may be operated as a single nozzle apparatus with only the above-mentioned components, e.g. for a radiation curing polymer.

In such use, the sprayhead 1 and electrode 11 are charged to the working potentials described hereinbefore, e.g. by connecting a high voltage generator or other high-tension D.C. source across the leads 19 and 12. The sprayhead high potential is preferably negative with respect to the field intensifying electrode 11. The electrode potential may be left to float, but this is much less preferred. Where the substrate 3 is a movable belt, it is set in motion.

The spraying fluid, e.g. a polymer or polymer precursor solution, is pumped from the reservoir 9 to the nozzle 2 where it atomizes to spray droplets 10 which are charged to a potential of the same sign as the nozzle 2 with respect to the substrate 3 and are attracted through the annular field intensifying electrode 18 towards the substrate. They solidify in flight, and the resultant solid particles impinge on and are collected on the substrate 3.

The use of the electrode 11 to control the spray pattern has been described hereinbefore, and the optional use of (an) auxiliary electrode(s) also for controlling the spray pattern is described below.

Where the fluid is a radiation solidifying material the apparatus is also provided with a radiation source 13, which as apt may be a uv lamp, an infra-red heater, or a hot gas stream, etc. to initiate (e.g.) reaction at the sprayhead 1 or in the spray 10.

The solidified particles from the spray pass down the chamber to impinge on and be collected on the collector substrate 3.

The spray chamber 14 in use serves to exclude undesirable drafts and/or to contain an inert, e.g. nitrogen, atmosphere which may be desirable for some reactive fluids. If desired the spray chamber 14 may be purged, and/or migration of the spray 10 to the substrate 3 slowed, by a gas stream within the chamber which is supplied to the container 14 by a duct 15 and vented via a mouth 17. The gas stream may advantageously assist any loss of vehicle from the spray 10, especially if warm, and such a warm or hot stream may be used as a thermal initiator.

Auxiliary electrode(s) (not shown) if used to control the undischarged or partly discharged spray may be mounted where apt, for example at the sides of the spraying region which contains the sprayhead 1 and substrate 3 and/or behind the substrate 3, generally in excess of 80 mm from the sprayhead 1.

By judicious choice of potential for example it or they may be used to focus the spray 10 away from the chamber walls. The chamber 14 may enclose, or itself be used, in whole or in part as, (an) auxiliary electrode(s)).

Although the foregoing embodiment has been described in terms of a straight downward flight path from a downwardly pointing nozzle, essentially under gravity, the apparatus may conveniently be used horizontally and in virtually any orientation in between, if it is provided with means to ensure that the product particles are collected as desired, for example auxiliary electrodes or supportive air masses or streams to keep the spray and/or particles on a desired flight path.

The substrate 3 is moved from the spraying region either continuously, or intermittently when a sufficient batch of particles has been collected, or the particles may be removed in batches from a stationary substrate 3.

Using further components described below, the apparatus of FIG. 1 may be used analogously for two component systems in a twin nozzle sprayhead. Thus in this embodiment the circular nozzle 2 is surrounded by a coaxial annular slot nozzle 22 as described hereinbefore, connected via a second line 27 with pump and second reservoir (28 and 29 not shown). Reservoirs 9 and 29 separately contain the two components. Delivery from the two nozzles 2,22 may conveniently be in a 1:1 volume rate ratio although any ratio which allows adequate reaction may be used.

In this case of course the radiation source 13 is unnecessary. In all other respects the spraying process is essentially as described for single-nozzle application.

FIG. 2 shows a two-sprayhead apparatus for the production of particles from the two components of a two component system. It will be seen that it is generally similar to the apparatus of FIG. 1, and the type of substrate 3 and its feed to the apparatus is the same.

The apparatus of FIG. 2, however, has two separate sprayheads 1 and 31 comprising conductive circular capillary nozzles 2 and 32 respectively, with sprayhead electrodes 18 and 48 mounted in conduits 17 and 47 and with charging means 19 and 49, and electrodes 11 and 41 with charging means leads 12 and 42 respectively. These are mounted far enough apart that in use there is no deleterions interaction of their electrostatic fields to earth. As shown they are mounted above and to either side of a conveyor belt substrate 3 and are aligned upon a favoured mixing region immediately above the substrate 3. Suitable arrangement of the sprayheads 1 and 31 for these purposes will be clear to the skilled man. In general maximum spatial separation of the sprayheads 1, 31 will tend to minimise undesirable field interactions.

Mixing of sprays 10 and 40 if of the same charge sign may not be entirely satisfactory. Accordingly, to achieve better mixing it may be desirable in use to have each sprayhead 10 and 40 of different polarity with respect to earth, provided that the application of the spray is not adversely affected thereby. Additionally the polarity of the sprayheads may be simultaneously reversed or alternated.

Other features of the apparatus, such as associated lines 7, 27, pumps 8, 38 and reservoirs 9, 39 for the two component fluids, and associated optional auxiliary electrodes and (all omitted) are essentially the same as in FIG. 1. There is of course no necessity for any radiation source 13.

Figure 2:
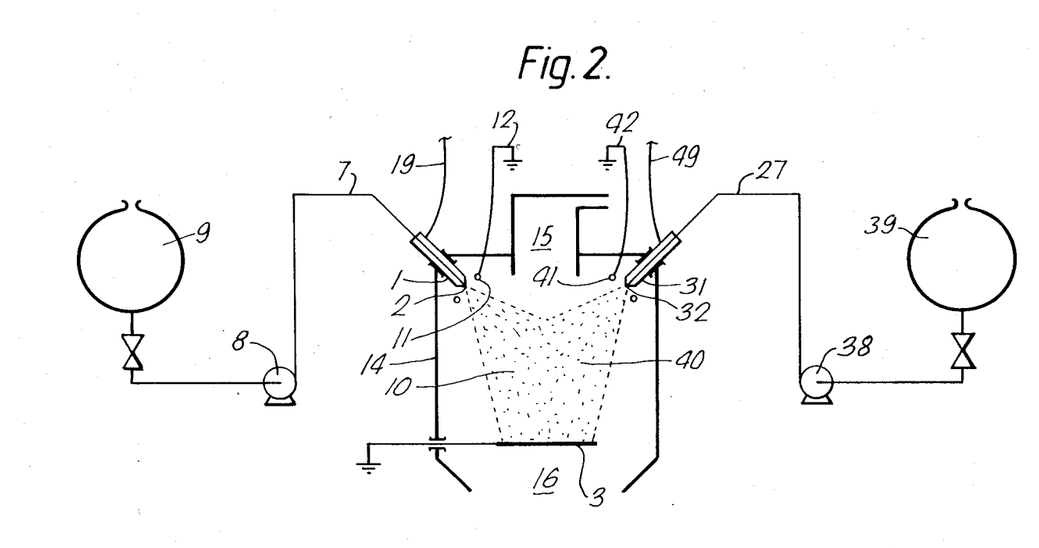

The use of the apparatus is essentially as described for FIG. 1 twin nozzle application.

Figure 3:
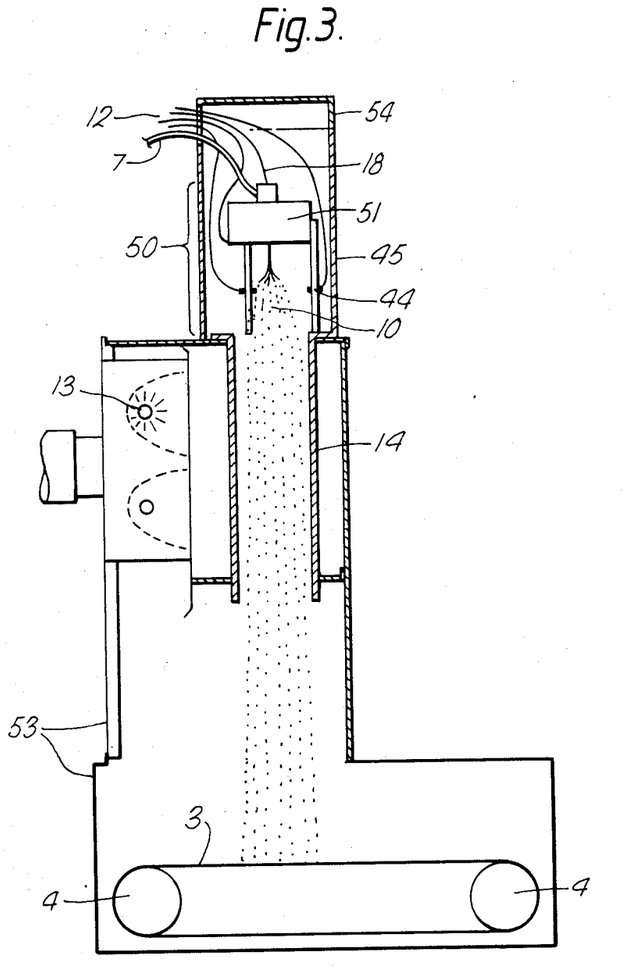

The apparatus shown in FIG. 3 is for the preferred process of the invention, which comprises the production of a charged spray and its discharge at least in part.

Figure 4:
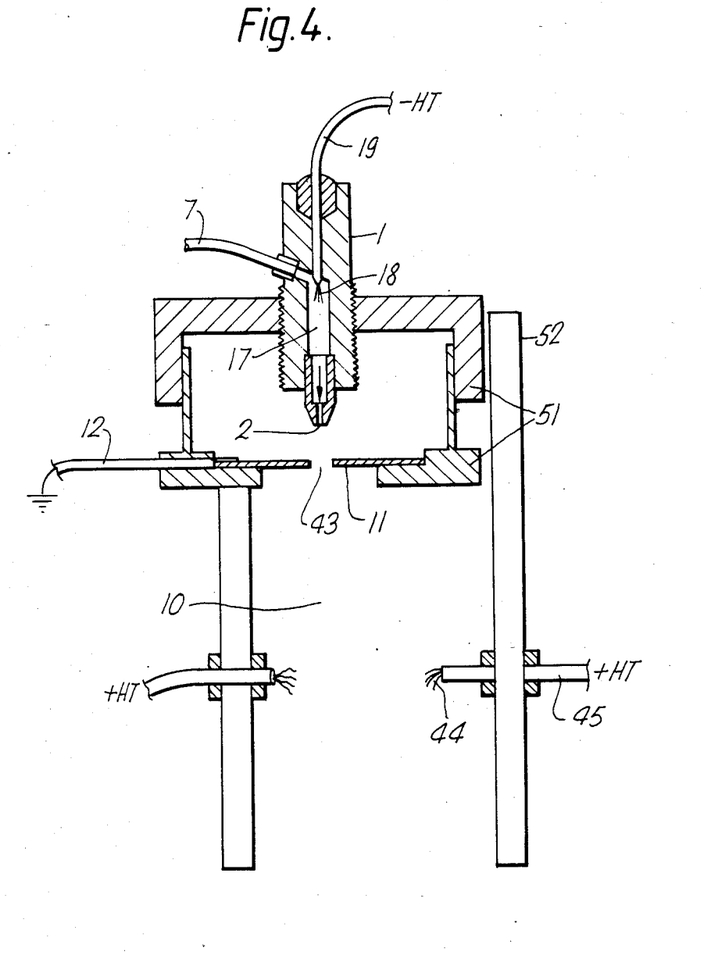

The apparatus comprises an assembly 50 fo the production of the at least partly discharged spray, which is shown in greater detail in FIG. 4. FIG. 4 is a full to half scale representation of a typical assembly 50 in a pilot or small scale apparatus of the present invention.

In FIGS. 3 and 4, the assembly 50 comprises a sprayhead 1 shield electrode 11 and a plurality of sharp discharge electrodes 54. The sprayhead 1 and shield electrode 11 are mounted in an assembly body 51 on tripod legs 52 connecting it to a housing 53; on the legs 52 the discharge electrodes 44 are mounted.

The sprayhead 1 comprises a feed conduit 17 running to a conductive circular nozzle 2 of the type described hereinbefore. Mounted coaxially with the nozzle 2 within the feed conduit 17 is a sprayhead electrode 18 with electrical lead 45, providing means to charge the sprayhead 1 to a first potential. The circular nozzle 2 may have a diameter in the range 0.15 to 3 mm, preferably 0.05 to 0.5 mm, to give flow rates of the order of 0.1 to 10 ml/min. The nozzle 2 may also (to increase throughput) be in the form of a linear slot up to about 3 m long of a cross section in the above range.

The annular plate shield electrode 11 is of 10 to 250 mm diameter and having a central circular orifice 43 is mounted at the base of the assembly body 51, coaxial with and about 5 to 25 mm below the nozzle 2. The assembly body 51 is telescopic to allow adjustment of this distance which is typically 2 to 40 mm.

Although here a plate, the electrode 11 may vary widely in shape, for example it may be a dish or globe providing it shields the sprayhead 1 from the corona discharge; it may for example also be or form part of a conduit for the spray. The shield electrode here consists of a conducting material (copper), but may also as described hereinbefore comprise a semi-conducting material optionally sheathing a conductive material. The semi-conductor may have a volume resistivity of $3\times10^2$ to $3\times10^4$ ohm. cm., and a dielectric strength greater than 8 KV/mm if used as a sheath. The shield electrode may have a thickness 0.75 to 5 mm, the foregoing is subject to the proviso that the total electrode has sufficient conductivity to remove in use any charge build-up due to the corona discharge.

The shield electrode is provided with an electrical lead 12 here running to earth, and providing means to charge the shield electrode to a second potential.

The central orifice 43 is sufficiently large that the fluid from the sprayhead 1 passes through without substantial deposition on the shield electrode 11, yet sufficiently small that the corona discharge does not pass through it, under the desired process conditions (see below).

The discharge electrodes 44 here consists of the cut and frayed ends of the wire strands of three multi-strand striaght high tension leads 45 connected in parallel, with one lead 45 bury mounted on and at right angles to each tripod leg 52, pointing towards the nozzle 2 axis, and slidable along the tripod leg 52 and its own length to adjust the shield electrode 11-discharge electrode 44 and axis discharge electrode 44 distances. The degree of spray discharge may be adjusted by means of such adjustments. Typically the shield electrode 11-discharge electrode 44 distance is 10 to 250 mm.

We have found that in practice that such multiple electrodes 44 are preferred for good discharge, and that their position off the spray axis permits good discharge whilst avoiding undue deposit of sprayed material on them. The shield electrode 11 and assembly body 51 enclose the sprayhead 1 from the discharge electrodes 44 except for the orifice 43 which is so dimensioned that in use the desired corona discharge does not pass through the orifice 43 into the interior of the assembly body 51.

We have found it always possible to select an orifice size which satisfactorily balances throughput against shielding. To some extent such selection is a matter of routine adjustment; however with flow rates in the range of 0.1 to 10 ml/min from a circular nozzle 2 such circular orifice diameters may suitably be in the range of 1 to 25 mm, for example 2 to 15 mm. Where the spray outlet is in the form of a linear slot up to about 3 m long it is believed that a corresponding slot in the shield electrode of a cross-section in the above range may be used at slot flow rates corresponding to the above nozzle flow rates.

The assembly 50 (preferably shrouded by a cap 54 e.g. of plastic) is mounted on a housing 53, containing an open ended cylindrical quartz spray chamber 14 mounted coaxial with the sprayhead nozzle 2 and shield electrode orifice 43 and a short distance below the discharge electrodes 44. Below the spray chamber's lower end, a flat collector substrate 3, which may be for example a conveyor belt strung between drums 4,4 (not shown) is mounted in the housing 53.

Sprayhead 1-substrate 3 distance may vary as described hereinbefore. However, the necessary process flight time will tend to be shorter than in the case of undischarged sprays and there will be less tendency for particles to approach the side walls of the spraying chamber. Thus, typically, the above distance may be in the range 0.3 to 30 m, and the spray chamber lateral dimensions may be in the range 4.5 mm to 8 m.

The cap 54, spray chamber 14 and housing 44 serve to exclude draughts and/or to contain the spray and/or particles when the apparatus is in use, as described further below.

The material of the spray chamber 14 (or any container for the discharged spray) is not crucial. However, where the spray is still charged to any appreciable extents after discharge and likely to contact the chamber walls it may be preferable that the chamber 14 is an earthed semi-conductor (c.f. the shield electrode 11) so that charge may leak to earth.

The nozzle 2 is connected via a line 7 containing pump 8 to a reservoir 9 for the material to be sprayed.

The apparatus for FIG. 3 may be operated as a single nozzle apparatus with only the above-mentioned components, e.g. a radiation curing polymer.

In such use, the sprayhead electrode 18, shield electrode 11 and discharge electrodes 44 are charged to the working potentials described hereinbefore.

(1) by connecting a high voltage generator or other first high-tension D.C source across the leads 19 and 12, to charge the sprayhead 1 to a high potential, preferably negative, with respect to the shield electrode 11, (and hence to charge any spraying fluid with the same polarity) and (2) by connecting another high voltage generator or other second high tension D.C. source across the leads 12 and 45 to charge the discharge electrodes 44 to a high potential of opposite polarity to that of the sprayhead (thus preferably positive) and high enough to discharge the spray at least partly.

The shield electrode potential may also be left to float, but this is much less preferred.

Where the substrate 3 is e.g. a moveable belt it is set in motion.

The spraying fluid, e.g. a polymer or polymer precursor solution, is pumped from the reservoir 9 to the nozzle 2 where it atomizes to spray droplets 10 which are charged to a potential of the same sign as the nozzle 2 with respect to the shield electrode 11 and pass through this annular electrode 11 towards the substrate 3. As the majority pass between the discharge electrodes 44 at least some of them are subject to corona discharge.

The solidification of the spray may be effected at any time in flight. Where the fluid is a radiation solidifying material the apparatus is suitably also provided with a radiation source 13, which as apt may be a uv lamp (as here), an infra-red heater, or a hot gas stream, etc to initiate solidification reaction at the sprayhead 1 or in the spray 10 before discharge or after discharge.

The embodiment depicted is set up to effect u.v. initiation of a curing reaction after spray discharge, by shining u.v. through the quartz side walls of the spray chamber 14.

The solidified particles from the spray pass down the chamber 14 to impinge on and be collected on to the collector substrate 3.

In use the cap 54, spray chamber 14 and housing 53 may contain an inert, e.g. nitrogen, atmosphere which may be desirable for some reactive fluids. If desired these containers may be purged, and/or migration of the spray 10 to the substrate 3 slowed by a gas stream within the chamber 14 which is supplied to the chamber 14 by a duct 15 and vented via a mouth 17 (not shown). The gas stream may advantageously assist any inert solvent loss from the spray 10, especially if warm, and such a warm or hot stream may be used as a thermal initiator.

Auxiliary electrode(s) 6 (not shown) if used to control the undischarged or partly discharged spray may be mounted where apt, for example at the sides of the spraying region which contains the chamber 14 and/or substrate 3 and/or behind the substrate 3, generally in excess of 80 mm from the sprayhead 1.

By judicious choice of potential for example it or they may be used to focus the spray 10 onto the substrate 3. (Where a chamber 14 is present, it may enclose, or be enclosed by, or itself be used, in whole or in part as, (an) auxiliary electrode(s)).

Although the foregoing embodiment has been described in terms of a straight downward flight path from a downwardly pointing nozzle, essentially under gravity, the apparatus may conveniently be used horizontally and in virtually any orientation in between, if it is provided with means to ensure that the product particles are collected as desired for example auxiliary electrodes or supportive air masses or streams to keep the spray and/or particles on a desired flight path.

The substrate 3 is moved from the spraying region either continuously or intermittently when a sufficient batch of particles has been collected, or the particles may be removed from the substrate 3 continuously or intermittently.

Although this embodiment of the apparatus of the present invention has been described for a single circular nozzle, a number of outlet orifices each with its own shield and discharge electrodes may be used in parallel, spraying into the same of different spray chambers if desired. Thus for example a bank of, say, 12 sprayheads or outlet orifices each up about 3 m long could it is believed produce 1,000 to 100,000 tonne of polymer beads per annum.

Using further components as described below the apparatus of FIG. 3 may be used analogously for two component systems in a twin nozzle sprayhead essentially the same as described in FIG. 1. Thus in this embodiment the circular nozzle 2 is surrounded by a coaxial annular slot nozzle 22 as described hereinbefore, connected via a second line 27 with pump 28 and second reservoir 29 (28 and 29 not shown). Reservoirs 9 and 29 separately contain the two components. Delivery from the two nozzles 2,22 may conveniently be in a 1:1 volume rate ratio although any ratio which allows adequate reaction may be used.

In this case of course the radiation source 13 is unnecessary. In all other respects the spraying process is essentially as described for a single-nozzle sprayhead 1.

Figure 5:
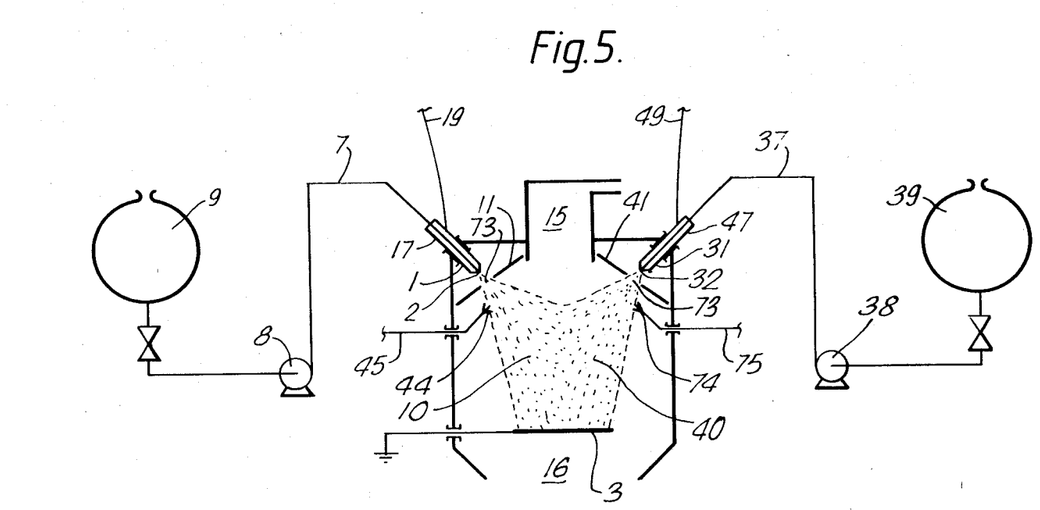

FIG. 5 shows a two-sprayhead apparatus for the production of particles from the two components of a two component system. It will be seen that it is generally similar to the apparatus of FIG. 3, and the type of substrate 3 and its feed to the apparatus is the same.

The apparatus of FIG. 5, however, has two separate sprayheads 1 and 31 comprising conductive circular capillary nozzles 2 and 32 respectively, with sprayhead electrodes 18 and 48 mounted in sprayhead conduits 17 and 47 with charging means leads 19 and 49, shield electrodes 11 and 41 with charging means leads 12 and 42 and orifices 43 and 73 respectively.

Often it is preferred that the two mixing sprays 10 and 40 are discharged to promote mixing; in such case the sprayheads will have separate discharge electrodes 44 and 74 with charging means leads 45 and 75 respectively as depicted in FIG. 5. These assemblies are mounted far enough apart that in use there is no deleterious interaction of their electrostatic fields to earth. As shown they are mounted above and to either side of a substrate 3 (here a conveyor belt) and are aligned upon a favoured mixing region well above the substrate 3.

Suitable arrangement of the sprayheads 1 and 31 for these purposes will be clear to the skilled man. In general maximum spatial separation of the sprayheads 1, 31 will tend to minimise undesirable field interactions.

Other features of the apparatus, such as associated lines 7, 37, pumps 8, 38 and reservoirs 9, 39 for the two component fluids, and associated optional auxiliary electrodes 6 and 36 (all omitted) are essentially the same as in FIG. 3. There is of course no necessity for any radiation source 13.

The use of the apparatus is essentially as described for FIG. 3 (twin nozzles).

The invention is further illustrated by the following Example:

Typical spray rates in the following Example are in the range of 1 to 3 $cm^3$/sec/mm of slot nozzle.

EXAMPLE

Solid, cured organic polymer beads (2–5 g) were obtained using the apparatus and process conditions described in relation to FIGS. 3 and 4 with u.v. photoinitiation, to spray into air the following four liquid materials, in each case with 2% w/w benzophenone-amine photoinitiator:

1. Urethane diacrylate (ICI), 42% w/w in a polyglycol diacrylate.

2. Photomer 4061 (tripropylene glycol diacrylate)
3. Photomer 4028 (aromatic diacrylate)
4. Photomer 4149 (aliphatic triacrylate)

We claim:

1. An apparatus for the production of solid particles by producing an electrically charged spray of fluid droplets of a narrow particle size distribution, by at least partial discharge of the spray, and by the solidifidation in flight of the droplets, the apparatus comprising:

a sprayhead with a channel for the fluid communicating with an outlet through which the fluid leaves the sprayhead in use;

an electrode, mounted on the sprayhead such that in use the electrode contacts the fluid before it leaves the sprayhead, and electrically connected with means for applying a first potential via the electrode to the fluid;

and a shield electrode mounted spaced from but adjacent to the sprayhead, having an orifice and electrically connected with means for applying a second potential to that electrode, a sharp discharge electrode, mounted spaced from but adjacent to the shield electrode such that the shield electrode lies between the sprayhead and the discharge electrode, and electrically connected with means for applying a third potential of opposite polarity to the first potential to the discharge electrode, such that in use the fluid is subjected to an electric field and moves from the sprayhead outlet under the influence of the field to produce a charged spray of the fluid, which issues through the orifice in the shield electrode towards the discharge electrode, the discharge electrode being so positioned that it can produce a corona discharge to discharge the spray, and the shield electrode and the orifice being so positioned and dimensioned as to shield the sprayhead from the corona.

2. An apparatus as in claim 1, for the production of solid particles from a mixture of a plurality of fluids, wherein the sprayhead has a plurality of channels for said fluids, each channel communicating with an outlet through which respective fluids leave the sprayhead in use, the outlets being so disposed that in use the fluids mix on or while moving from the sprayhead, and wherein the electrode is mounted on the sprayhead such that in use the electrode contacts at least one fluid before it leaves the sprayhead.

3. An apparatus as in claim 1, which comprises a plurality of sharp discharge electrodes.

4. Apparatus for the production of a spray of fluid droplets of a narrow particle size distribution by providing an electrically charged spray and at lest partially discharging the spray, comprising: a sprayed with a channel for the fluid communicating with an outlet through which the fluid leaves the sprayhead in use;

an electrode, mounted on the sprayhead such that in use the electrode contacts the fluid before it leaves the sprayhead, and electrically connected with means for applying a first potential via the electrode to the fluid; and a shield electrode mounted spaced from but adjacent to the sprayhead, having an orifice electrically connected with means for applying a second potential to that electrode, a sharp discharge electrode, mounted spaced from but adjacent to the shield electrode such that the shield electrode lies between the sprayhead and the discharge electrode, and electrically connected with means for applying a third potential of opposite polarity to the first potential to the discharge electrode, such that in use the fluid is subjected to an electric field and moves from the sprayhead outlet under the influence of the field to produce a charged spray of the fluid, which issues through the orifice in the shield electrode towards the discharge electrode, the discharge electrode being so positioned that it can produce a corona discharge to discharge the spray, and the shield electrode and the orifice being so positioned and dimensioned as to shield the sprayhead from the corona.

5. An apparatus as in claim 4, for the production of solid particles from a mixture of a plurality of fluids, wherein the sprayhead has a plurality of channels for said fluids, each channel communicating with an outlet through which respective fluids leave the sprayhead in use, the outlets being so disposed that in use the fluids mix on or while moving from the sprayhead, and wherein the electrode is mounted on the sprayhead such that in use the electrode contacts at least one fluid before it leaves the sprayhead.

6. As apparatus as in claim 4, which comprises a plurality of sharp discharge electrodes.

* * * * *